United States Patent
Aparin et al.

(10) Patent No.: US 8,951,538 B2
(45) Date of Patent: *Feb. 10, 2015

(54) **EXOPOLYSACCHARIDE OF *SHIGELLA SONNEI* BACTERIA, METHOD FOR PRODUCING SAME, VACCINE AND PHAMACEUTICAL COMPOSITION CONTAINING SAME**

(71) Applicants: Petr Gennadievich Aparin, Odintzovo (RU); Vyacheslav Leonidovich Lvov, Moscow (RU); Stanislava Ivanovna Elkina, Moscow (RU); Marina Eduardovna Golovina, Moscow (RU); Vladimir Igorevich Shmigol, Moscow (RU)

(72) Inventors: Petr Gennadievich Aparin, Odintzovo (RU); Vyacheslav Leonidovich Lvov, Moscow (RU); Stanislava Ivanovna Elkina, Moscow (RU); Marina Eduardovna Golovina, Moscow (RU); Vladimir Igorevich Shmigol, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,522

(22) Filed: Apr. 2, 2013

(65) Prior Publication Data

US 2014/0037687 A1    Feb. 6, 2014

(51) Int. Cl.
*A61K 39/02*    (2006.01)
*A61K 45/00*    (2006.01)
*A61K 39/00*    (2006.01)
*A61K 39/112*   (2006.01)
*A61K 47/00*    (2006.01)

(52) U.S. Cl.
CPC ............ *A61K 39/0283* (2013.01); *A61K 47/00* (2013.01)
USPC ................... 424/234.1; 424/93.1; 424/184.1; 424/193.1; 424/278.1; 435/41

(58) Field of Classification Search
USPC ............ 424/93.1, 184.1, 193.1, 234.1, 278.1; 435/41
See application file for complete search history.

(56) References Cited

PUBLICATIONS

Lennart Kenne et.< Structural studies of the o-specific side-chains of the *Shigella sonnei* phase I lipopolysaccharide. Carbohydrate Research, 1980, 78(1), pp. 119-126.
John B. Robbins et. al., Synthesis, characterization, and immunogenicity in mice of *Shigella sonnei* O-specific oligosaccharide-core-protein conjugates. Proc Natl Acad Sci, Jan. 27, 2009, [found Dec. 28, 2011], found on inetrnet<URL:http//www.pnas./cgi/doi/10.1073/pnas.0900891106>, p. 1-5.

*Primary Examiner* — Rodney P Swartz
(74) *Attorney, Agent, or Firm* — Nadya Reingand; Yan Hankin

(57) ABSTRACT

For the first time, an O-specific polysaccharide antigen that is a *Shigella sonnei*, phase I, exopolysaccharide has been produced and characterized, said exopolysaccharide being an authentic natural compound in the form of a bacterial capsular polysaccharide. The exopolysaccharide contains a nontoxic lipid component, namely non-hydroxylated fatty acids, and exhibits low pyrogenicity and high immunogenicity. Effective, highly specific and safe vaccines for the prophylaxis and/or treatment of *Shigella sonnei* shigellosis are developed on the basis of the above-mentioned exopolysaccharide, as well as pharmaceutical compositions with a broad spectrum of action, in particular, in modulating immune response.

16 Claims, 5 Drawing Sheets

Figure 1:
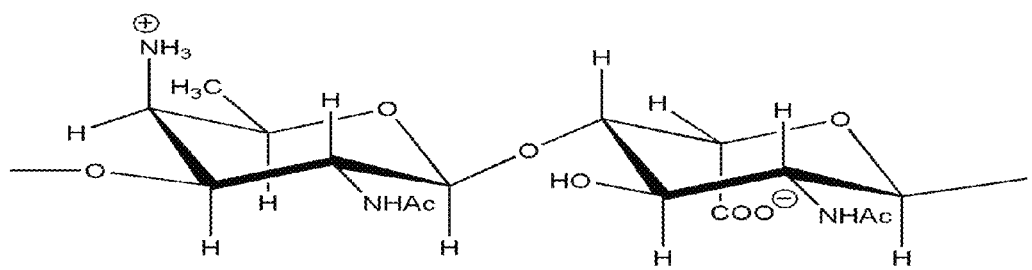

EXOPOLYSACCHARIDE OF *SHIGELLA SONNEI* BACTERIA, METHOD FOR PRODUCING SAME, VACCINE AND PHAMACEUTICAL COMPOSITION CONTAINING SAME

CROSS-REFERENCE TO RELATED APPLICATIONS

This application claims priority to PCT patent application PCT/RU2011/000314 filed May 6, 2011. It is also a Continuation-in-part of the U.S. patent application Ser. No. 13/877,305 filed Apr. 1, 2013.

FIELD OF INVENTION

The invention relates to the clinical immunology and pharmacology, in particular it relates to the polysaccharide antigen of the bacteria *Shigella sonnei*, phase I—O-specific exopolysaccharide, the method of obtaining it, and the vaccine and pharmaceutical composition comprising it.

BACKGROUND OF THE INVENTION

Almost 100 years now after discovering the *bacillus* Shiga, commonly known as *Shigella dysenteriae*, type 1, shigellosis is the one of the most important public health problems of almost all countries in the world. Annually, several hundred thousand children under the age of 5 die in developing countries from shigellosis caused by microorganisms of the genus *Shigella*. Outbreaks of shigellosis are occasionally registered in developing countries of the northern hemisphere, caused by the bacteria *S. sonnei*, the only representative of group D, genus *Shigella*.

Relating to the aforementioned, WHO recommends as a priority goal the development of a "global" anti-*shigella* vaccine, including protective compounds for pathogenic bacteria of genus *Shigella*, specifically *S. sonnei*, phase I (Kotloff K. L., Winickoff J. P, Ivanoff B., Clemens J. D., Swerdlow D. L., Sansonetti P. J., Adak G. K., Levine M. M. Global burden of *Shigella* infections: implications for vaccine development and implementation of control strategies. Bull. WHO, 1999, v. 77, p. 651-665). Development of a monovaccine against shigellosis *S. sonnei* may be considered as a preliminary step for the solution of this general problem and as an independent project extremely actual for many regions.

The specificity of immunity to *Shigella* infection is determined by the structure of the *Shigella*'s main protective antigen—the polysaccharide O-antigen. The primary structure of O-specific polysaccharide obtained from the lipopolysaccharide (LPS) molecule of cell walls of *S. sonnei*, phase I is identified by Kenne et al. (Kenne L., Lindberg B., Petersson K., Katzenellenbogen E., Romanowska E. Structural studies of the O-specific side-chains of the *Shigella sonnei* phase I lipopolysaccharide. Carbohydrate Res., 1980, 78:119-126).

The O-antigen component of LPS is a polysaccharide composed of repeating disaccharide units of O-[4-amino-2-(N-acetyl)amino-2,4-dideoxy-β-D-galactopyranosyl]-(1→4)-[2-(N-acetyl)amino-2-deoxy-α-L-altrpyranuronic acid] linked by (1→3) bonds to form a polysaccharide chain. This O-polysaccharide component of *S. sonnei*, phase I, covalently links to *E. coli* R2 type core domain, which, in turn, covalently links to lipid A forming a linear molecule LPS.

Isolation of O-polysaccharide from the cell wall LPS does not represent significant technical difficulties. Thus, the method of isolation, first proposed by Freeman, includes the following main stages—obtaining a culture of bacteria *S. sonnei*, phase I in liquid medium; separation of culture fluid from bacterial cells, extracting LPS from bacterial cell with aqueous phenol (Westphal O., Jann K. Bacterial lipopolysaccharide extraction with phenol: water and further application of the procedure. Methods Carbohydr. Chem., 1965, v. 5, p. 83-91); and degradation of LPS with further isolation of the O-polysaccharide from it (Morrison D. C., Leive L. Fractions of lipopolysaccharide from *Escherichia coli* O111:B4 prepared by two extraction procedures. J. Biol. Chem. 250 (1975) 2911-2919).

Another method of obtaining highly purified O-specific antigen of *Shigella* sp is also known and includes the following stages: obtaining bacterial cultures in liquid medium; treatment of bacterial cultures with hexadecyltrimethylammonium bromide and subsequent extraction of LPS from bacterial cells; separation of LPS extract from bacterial cells; and degradation of LPS with subsequent separation of O-polysaccharide from it (KR 20010054032 A). Thereby, all known methods of isolating O-specific antigens from *Shigella* sp. LPS are based on the stage of extraction, i.e. LPS extraction from bacterial cell walls, which causes the unavoidable loss of bacterial cell nativity.

It should be additionally noted, that the structure of O-specific antigens obtained by known methods from LPS's is determined by the genomes of *Shigella* sp bacteria.

Practically all O-antigens obtained from *Shigella* sp. LPS's contain elements of core domain structures. Mild hydrolysis using 1% acetic acid, which is used for removal of lipid A from the LPS molecule, leads to obtaining a polysaccharide derivative, which is represented as an O-specific polysaccharide, connected to the "core" oligosaccharide (Fensom and Meadow 1970; Morrison and Leive, 1975; Oertelt et al., 2001; Osborn, 1963.

It was proposed to use the O-polysaccharide from the LPS of the bacterial cell wall of *S. sonnei*, phase I, as a component of only conjugated vaccines against *S. sonnei* shigellosis, under its covalent bonding with protein carriers—protein D *Haemophilis influenzae*, recombinant exoprotein A *Pseudomonas aeruginosa* (rEPA), recombinant diphtheria toxin (rDT), recombinant toxin B *Clostridium difficle* (rBRU) (US Pat. Appl. 2005/0031646; WO/2010/019890).

Investigations were conducted of the immunogenic and protective properties of conjugates containing O-polysaccharide from the LPS of the bacterial cell walls of *Plesiomonas shigelloides* O7, whose structure is identical to O-polysaccharide from LPS of bacteria *S. sonnei*, phase I, and conjugated with protein—exoprotein A *P. aeruginosa* (rEPA) or diphtheria toxoid CRM9 from mutant strain *Corynebacterium diphtheriae* (Cohen D., Ashkenazi S., Green M. S., Gdalevich M., Robin G., Slepon R., Yavzori M., Orr N., Block C., Ashkenazi I., Shemer J., Taylor D. N., Hale T. L., Sadoff J. C., Pavliakova D., Schneerson R., Robbins R. Double-blind vaccine controlled randomized efficacy trial of an investigational *Shigella sonnei* conjugate vaccine in young adults. Lancet, 1997, v. 349, pp. 155-159). It has been found that the conjugate of O-polysaccharide with rEPA was immunogenic for experimental animals and humans when administered parenterally, causing in volunteers O-specific antibody production and average level of protection against infection with an efficacy coefficient of 74%. However, the rather short duration of the controlled experiment (2.5-7 months) is causing certain doubts in the rating for the protective potential of the vaccine. Recent immunogenicity trials on children of O-polysaccharide conjugate vaccine against *S. sonnei* infection based on rEPA-carrier revealed low immunogenicity of the preparation for children of ages from 1 to 4 years (efficacy coefficient was 27.5%), as well as the early declining of immune response after immunization (Passwell J H, Ashkenzi S, Banet-Levi Y, Ramon-Saraf R, Farzam N, Lerner-Geva L, Even-Nir H, Yerushalmi B, Chu C, Shiloach J, Robbins J B, Schneerson R; Israeli Shigella Study Group. Age-related efficacy of *Shigella* O-specific polysaccharide conjugates in 1-4-year-old Israeli children. Vaccine. 2010, March, 2; 28(10), pp. 2231-2235).

Thus, the protein-polysaccharide conjugate vaccines against shigellosis *S. sonnei* have shown an insufficient immunogenicity in clinical trials on adults and children. It should be noted that the immunogenic properties of free, unconjugated O-polysaccharide from the LPS of the *S. sonnei* bacteria, phase I, as a vaccine immunogen is not known. Experimental data from Taylor et al show a practically full absence of immunogenic activity in mice against unconjugated polysaccharide from LPS of bacterial cells *Plesiomonas shigelloides*, the structure of which is identical to that of *S. sonnei*, phase I O-antigen (Taylor D. N., Trofa A. C., Sadoff J., Chu C., Bryla D., Shiloach J., Cohen D., Ashkenazi S., Lerman Y., Egan W. Synthesis, characterization and clinical evaluation of conjugate vaccines composed of the O-specific polysaccharides of *Shigella dysenteriae* type 1, *Shigella flexneri* type 2a, and *Shigella sonnei* (*Plesiomonas shigelloides*) bound to bacterial toxoids. Infect. Immun., 1993, September, 61(9): 3678-3687).

Based on the aforementioned, the actuality of development of other approaches to the creation of O-antigen vaccines against *S. sonnei* infection is obvious. An alternative, and more promising approach for development can be considered: the creation of an unconjugated vaccine based on the O-antigen exopolysaccharide, produced by *S. sonnei*, phase I bacteria into the cultural medium. It is known, that many gram-positive and gram-negative bacteria produce not only polysaccharide components of cell walls, but also extracellular exopolysaccharides, which are secreted by the cell into the external medium and provide the protective function. Thus, the produced exopolysaccharides can be found both in a free state or form an extracellular capsule or microcapsule.

Sometimes exopolysaccharides produced by cells into the external medium represent specific highly-immunogenic antigens—capable of inducing protective antibody synthesis. Thus, a variety of such polysaccharide antigens are used in the vaccine compositions for prevention of infections, caused by meningococcus groups A and C, cause of typhoid fever (Lindberg A. A. Polyosides (encapsulated bacteria). C. R. Acad. Sci. Paris, 1999, v. 322, p. 925-932).

Polysaccharide vaccine immunogenicity is dependent on the primary structure of the polysaccharide antigen, its molecular mass, and ability to form aggregate structures (The vaccine book. Edited by B. R. Bloom, P.-H. Lambert Academic Press, San Diego 2003, pp. 436). At the same time, the primary structure of bacterial exopolysaccharide can be identical to or different from that of O-specific polysaccharide from the cell wall LPS. (Goldman R. C., White D., Orskov F., Orskov I., Rick P. D., Lewis M. S., Bhattacharjee A. K., Leive L. A surface polysaccharide of *Esherichia coli* O111 contains O-antigen and inhibits agglutination of cells by anti-O antiserum. J. Bacteriol., 1982, v. 151, p. 1210-1221).

However, neither the primary structure of the exopolysaccharide of bacteria *S. sonnei*, phase I, nor its physico-chemical, immunobiological, and protective properties, nor the method of its isolation, nor even the fact of its existence are described in the literature.

The literature also does not describe the pharmaceutical compositions based on *S. sonnei*, phase I polysaccharides, the development of which can make significant contributions to clinical pharmacology. Only known is the usage of fragments of polysaccharides from LPS of *S. sonnei*, phase I cells, including from 1 to 5 disaccharide units, as a nutrient supplement for oral administration, stimulating immune system development in infants between 1 and 6 months of age, determined by the increase of ratio of type 1 T-helpers (Th1 response) in relation to the type 2 T-helpers (Th2 response) ratio (US Pat. Appl. 2009/0317427 A1).

SUMMARY OF THE INVENTION

The claimed invention provides, through a high-tech method, exopolysaccharides of bacteria *S. sonnei*, phase I, and discloses on its basis polysaccharide vaccines and pharmaceutical compositions.

The technical results, provided by the claimed invention, include but are not limited to: (a) obtaining native polysaccharide from *S. sonnei*, phase I bacteria of high purity with a high yield on a commercial scale; (b) increasing the specificity, immunogenicity, protective activity and safety of developed vaccines; and (c) high efficacy and broad spectrum of activity of the proposed pharmaceutical compositions.

Obtained for the first time is a new polysaccharide antigen—exopolysaccharide, or capsular polysaccharide, secreted by *S. sonnei*, phase I bacteria into the external medium. In contrast to O-specific polysaccharide from LPS bacterial cell wall, an artificially isolated fragment of the molecule, the exopolysaccharide is an authentic natural compound, derived using *S. sonnei* bacteria, but without the use of LPS as its source. The primary structure of the exopolysaccharide is identical to that of the O-polysaccharide from LPS of bacteria *S. sonnei*, phase I, i.e. the exopolysaccharide consists of 1-100 repeating disaccharide units of O-[4-amino-2-(N-acetyl)amino-2,4-dideoxy-β-D-galactopyranosyl]-(1→4)-O-[2-(N-acetyl)amino-2-deoxy-α-L-altrpyranuronic acid] connected by (1→3) bonds to form a polysaccharide chain (FIG. 1 and FIG. 2). In contrast to the O-polysaccharide from bacterial cell LPS, the native exopolysaccharide includes a non-toxic lipid component, the composition of which contains non hydroxylated fatty acids with 16-18 carbon atoms in the molecule (FIG. 3, FIG. 4). The fatty acid content in it is no less than 0.01 (w/w) percent. Additionally, obtained by any method, the exopolysaccharide from *S. sonnei* bacteria does not include elements of LPS core domain structure (FIG. 4). Exopolysaccharide can be prepared by any method, including genetic engineering, using the genome of *S. sonnei* bacteria. Preferably the exopolysaccharide is produced using *S. sonnei* bacteria by a method, comprising: (a) production of the bacterial culture in liquid phase; (b) separating the liquid phase from bacterial cells; and (c) isolating the polysaccharide from liquid phase. Meanwhile, to avoid destroying the cell wall and LPS entry into the liquid phase, separating it from the bacterial cells is advisable to preserve the nativity of bacterial cells. Isolating the polysaccharide from the liquid phase can be carried out by a method, comprising: (i) removing proteins and nucleic acids from the liquid phase; (ii) ultrafiltration, and (iii) dialysis of obtained solution.

Obtained using the above method, exopolysaccharide contains no more than 1% (w/w) of protein and 2% (w/w) of nucleic acid. The molecular weight of the exopolysaccharide, measured by gel filtration, is from 0.4 to 400 kDa. The main fraction of the exopolysaccharide is a biopolymer with molecular weight over 80 kDa (FIG. 5B), while the main fraction of O-polysaccharide has a molecular weight of not more than 26 kDa (FIG. 5A). Exopolysaccharide is immunogenic and causes mucosal protection from shigellosis *S. sonnei* by inducing synthesis of specific antibodies against *S.*

Figure 6:
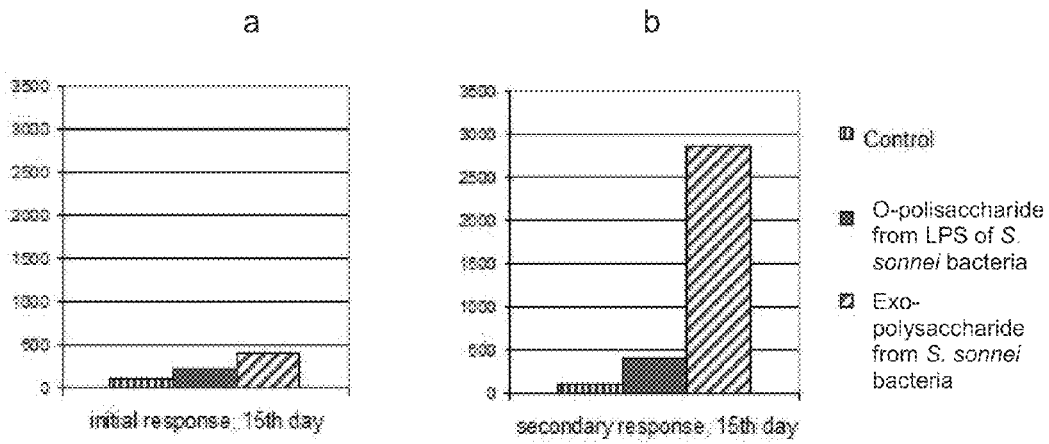
Figure 7:
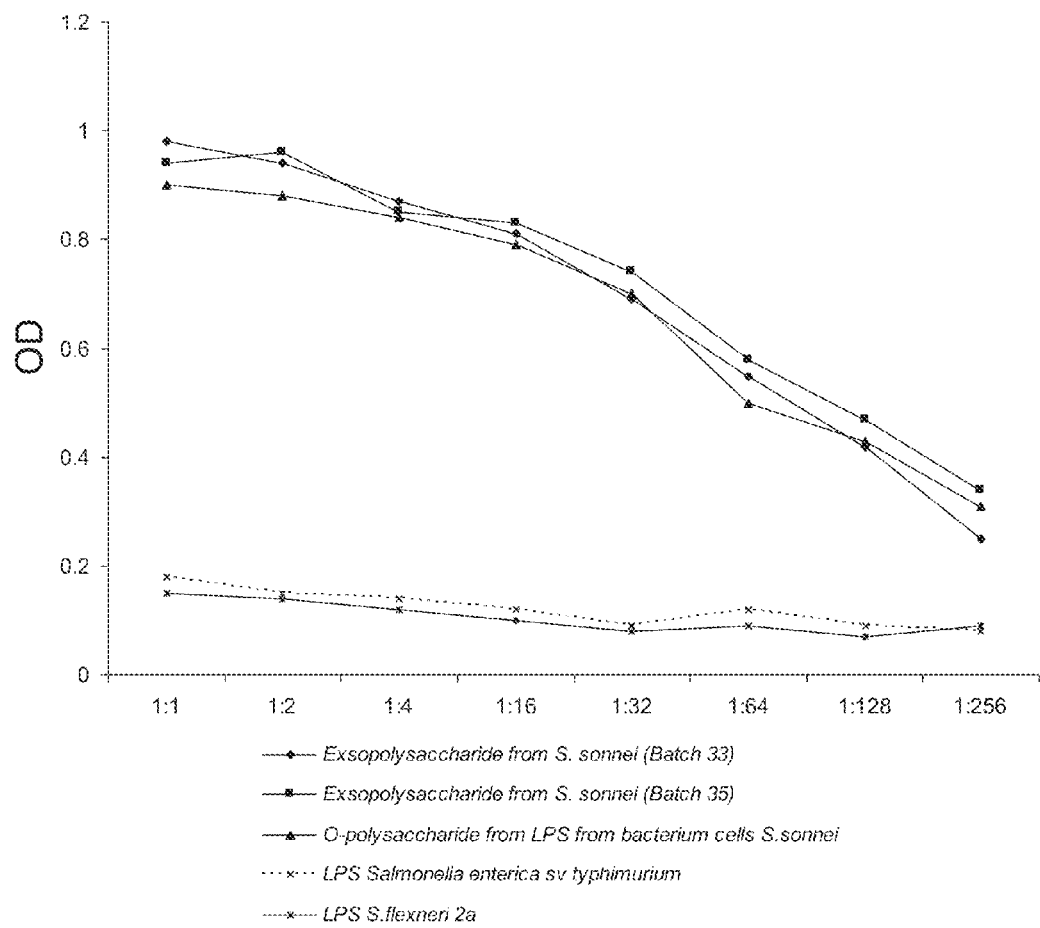

*sonnei*, phase I bacteria in mammalian organisms, including humans (Example 1C, FIG. 6; Examples 2D, 2F).

As noted above, the immunogenicity of the polysaccharide antigen is determined by its molecular weight and ability to form aggregate structures, so the highest immunogenicity is found out for exopolysaccharide fraction with molecular weight from 80 to 400 kD. Immunogenicity of the high molecular weight fraction of the exopolysaccharide exceeds more than 7 times the immunogenicity of the O-polysaccharide from bacterial cells LPS (Example 1C, FIG. 6), which is apparently determined by the presence in the molecule of a non-toxic lipid component—a non hydroxylated fatty acid contributing to supramolecular aggregate structure formation.

Additionally, the exopolysaccharide is apyrogenic for rabbits when administered intravenously at a dose of no more than 0.050 mcg/kg in a rabbit pyrogenicity test (Example 1D). Exopolysaccharide vaccine formulation meets WHO Expert Committee requirements for polysaccharide vaccines pyrogenicity parameter (WHO TR—WHO Technical report No. 840, 1994).

Figure 5:
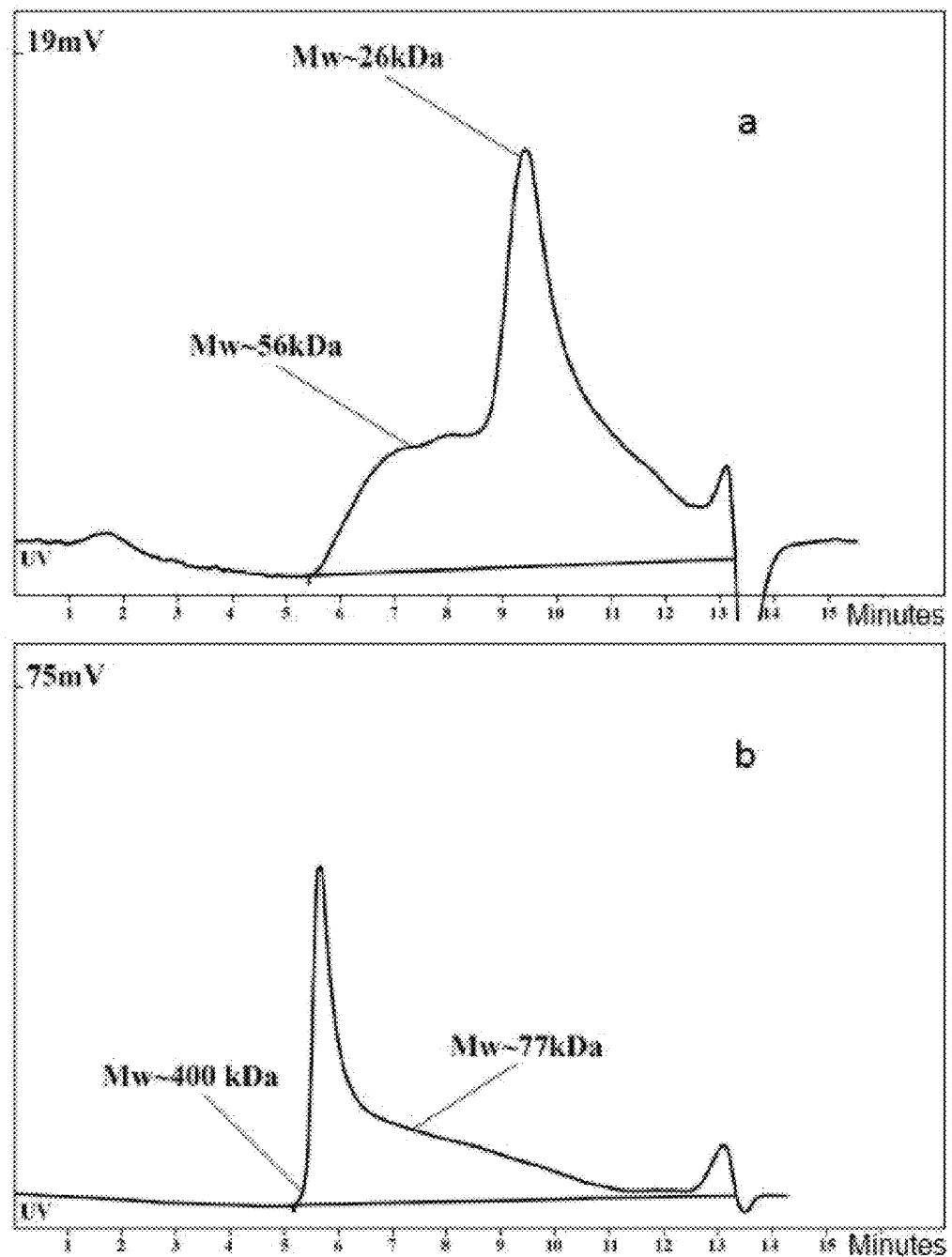

The claimed method for producing *S. sonnei*, phase I bacteria exopolysaccharide comprises: (a) producing cultures of *S. sonnei* bacteria in liquid phase; (b) separating liquid phase from bacterial cells; and (c) isolating polysaccharide from liquid phase. At the same time, the liquid phase, which maintains cell cultures viability, can be represented by a nutrient environment having various compositions and properties. Separating liquid phase from bacterial cells is preferably carried out while maintaining nativity of bacterial cells.

Thus, the claimed method for producing a polysaccharide, which excludes the use of LPS as its source, does not contain the stage of LPS extraction from bacterial cell walls normally resulting in the inevitable loss of bacterial cell nativity.

Isolation of polysaccharide from liquid phase can be carried out by a method comprising: (i) removal of proteins and nucleic acids from liquid phase; (ii) ultrafiltration and (iii) dialysis of obtained solution.

The claimed vaccine for prophylaxis and/or treatment of *S. sonnei* shigellosis contains prophylactically and/or therapeutically effective amounts of *S. sonnei*, phase I bacteria polysaccharides, consisting of 1-100 repeating disaccharide units of O-[4-amino-2-(N-acetyl)amino-2,4-dideoxy-β-D-galactopyranosyl]-(1→4)-O-[2-(N-acetyl)amino-2-deoxy-α-L-altrpyranuronic acid] connected by (1→3) bonds to form a polysaccharide chain, and obtained using *S. sonnei* bacteria, but without the use of lipopolysaccharides as its source.

This polysaccharide is an exopolysaccharide, or capsular polysaccharide, secreted into the external medium by *S. sonnei*, phase I bacteria. The native exopolysaccharide includes a non-toxic lipid component, presented by non hydroxylated fatty acids from 16-18 carbon atoms in the molecule (FIG. 4). Its fatty acid content is not less than 0.01% (w/w). Additionally, independently from the method of preparation with use *S. sonnei* bacteria, the exopolysaccharide does not include elements of the structure of LPS core domain (FIG. 4).

Exopolysaccharide can be prepared by any method, including genetic engineering, using the genome of *S. sonnei* bacteria. Preferably the exopolysaccharide is produced using *S. sonnei* bacteria by a method comprising: (a) producing bacterial culture in liquid phase; (b) separating the liquid phase from bacterial cells; and (c) isolating the polysaccharide from liquid phase. Meanwhile, in order to avoid destroying the cell walls and LPS entry into the liquid phase, separation from the bacterial cells is advisable to carry out under conditions for maintaining the nativity of bacterial cells. Isolating the polysaccharide from the liquid phase can be carried out by a method, comprising: (i) removing proteins and nucleic acids from the liquid phase; (ii) ultrafiltration, and (iii) dialysis of obtained solution.

Obtained using the above method exopolysaccharide contains no more than 1% (w/w) of protein and 2% (w/w) of nucleic acid. The molecular weight of the exopolysaccharide, which is measured by gel filtration, is from 0.4 to 400 kDa. The main fraction of the exopolysaccharide is a biopolymer with molecular weight over 80 kDa (FIG. 5B).

Exopolysaccharide is immunogenic and causes mucosal protection from *S. sonnei* shigellosis by inducing synthesis of specific antibodies against *S. sonnei*, phase I bacteria in mammalian organisms, including humans (Example 1C, FIG. 6; Examples 2D, 2F).

The highest immunogenicity is found for exopolysaccharide fraction with molecular weight from 80 to 400 kDa. Immunogenicity of the exopolysaccharide increases more than 7 times the immunogenicity of the O-polysaccharide from bacterial cell LPS (Example 1C, FIG. 6). The exopolysaccharide is apyrogenic for rabbits when administered intravenously at a dose of no more than 0.050 mcg/kg in a rabbit pyrogenicity test (Example 1D).

The claimed vaccine may comprise pharmaceutically acceptable additives, which may include pH stabilizers, preservatives, adjuvants, isotonizing agents, or combinations thereof. This vaccine may include exopolysaccharides in conjugated as well as unconjugated form. Meanwhile, the vaccine, comprised of the conjugated form of the exopolysaccharide, also contains a carrier protein, namely diphtheria toxoid or tetanus toxoid, or *P. aeruginosa* protein A, or other proteins.

The claimed pharmaceutical composition contains effective amounts of *S. sonnei*, phase I bacteria polysaccharides, consisting of 1-100 repeating disaccharide units of O-[4-amino-2-(N-acetyl)amino-2,4-dideoxy-β-D-galactopyranosyl]-(1→4)-O-[2-(N-acetyl)amino-2-deoxy-α-L-altrpyranuronic acid] connected by (1→3) bonds to form a polysaccharide chain, and obtained using *S. sonnei* bacteria, but without the use of lipopolysaccharides as its source.

This polysaccharide is an exopolysaccharide, or capsular polysaccharide, secreted into the external medium by *S. sonnei*, phase I bacteria. The native exopolysaccharide includes a non-toxic lipid component, presented by non hydroxylated fatty acids from 16-18 carbon atoms in the molecule (FIG. 4). Its fatty acid content is not less than 0.01% (w/w). Additionally, independently from the method of preparation with use *S. sonnei* bacteria, the polysaccharide does not include elements of the structure of LPS core domain (FIG. 4).

Exopolysaccharide can be prepared by any method, including genetic engineering, using the genome of *S. sonnei* bacteria. Preferably the exopolysaccharide is produced using *S. sonnei* bacteria by a method, comprising: (a) producing bacterial culture in liquid phase; (b) separating the liquid phase from bacterial cells; and (c) isolating the polysaccharide from liquid phase. Meanwhile, in order to avoid destroying the cell walls and LPS entry into the liquid phase, separation from the bacterial cells is advisable to carry out under conditions for maintaining the nativity of bacterial cells. Isolating the polysaccharide from the liquid phase can be carried out by a method, comprising: (i) removing proteins and nucleic acids from the liquid phase; (ii) ultrafiltration, and (iii) dialysis of obtained solution.

The exopolysaccharide obtained by using the above method can contain no more than 1% (w/w) of protein and 2% (w/w) of nucleic acid. The molecular weight of the exopolysaccharide, which is measured by gel filtration, is varied from 0.4 to 400 kDa. The main fraction of the exopolysaccharide is a biopolymer with molecular weight over 80 kDa (FIG. 5B).

Exopolysaccharide is the immune system response modulator in mammals, including humans (Example 3B). The exopolysaccharide is apyrogenic for rabbits when administered intravenously at a dose of no more than 0.050 mcg/kg in a rabbit pyrogenicity test (Example I D).

The claimed pharmaceutical composition may comprise pharmaceutically acceptable targeted additives, which may include preservatives, stabilizers, solvents, or combinations thereof.

Figure 9:
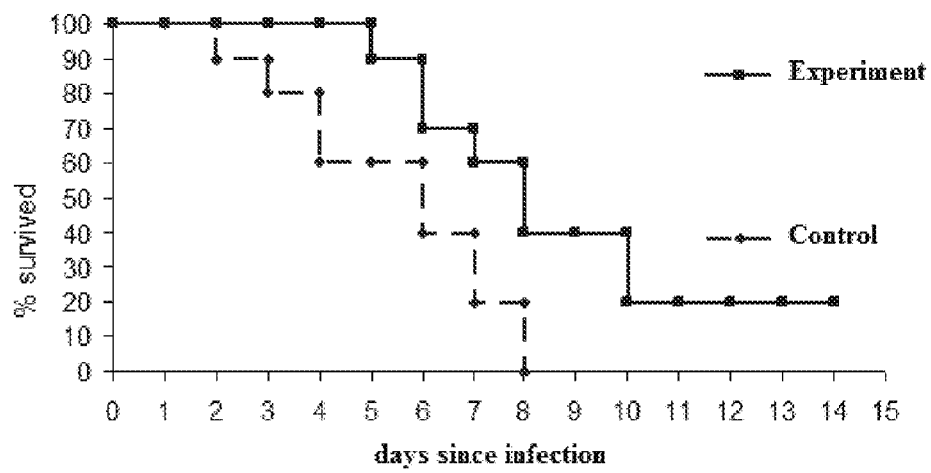

The claimed pharmaceutical composition can have a wide range of pharmacological activity and exhibits, in particular, an effective therapeutic antiviral effect under infection caused by influenza A virus subtype H1N1 (Example 3B, FIG. 9)

Also claimed is the use of polysaccharide from S. sonnei, phase I bacteria for production of vaccine or pharmaceutical composition. The stated polysaccharide consists of 1-100 repeating disaccharide units of O-[4-amino-2-(N-acetyl) amino-2,4-dideoxy-β-D-galactopyranosyl]-(1→4)-O-[2-(N-acetyl)amino-2-deoxy-α-L-altrpyranuronic acid] connected by (1→3) bonds to form a polysaccharide chain, and obtained using S. sonnei bacteria, but without the use of lipopolysaccharides as its source.

Figure 4:
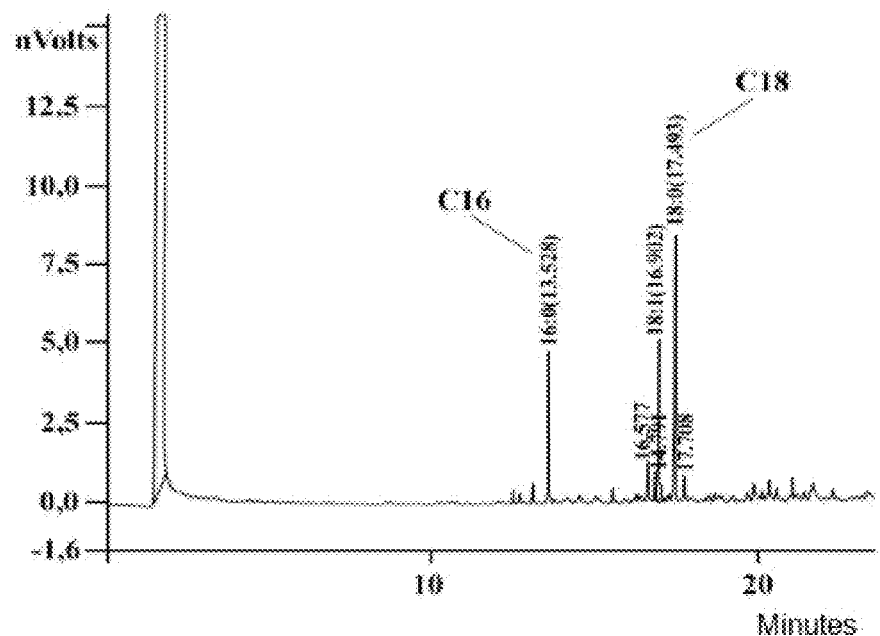

This polysaccharide is an exopolysaccharide, or capsular polysaccharide, secreted into the external medium by S. sonnei, phase I bacteria. The native exopolysaccharide includes a non-toxic lipid component, presented by non hydroxylated fatty acids from 16-18 carbon atoms in the molecule (FIG. 4). Its fatty acid content is not less than 0.01% (w/w). Additionally, independently from the method of preparation with S. sonnei bacteria, the exopolysaccharide does not include elements of the structure of LPS core domain (FIG. 4).

Exopolysaccharide can be prepared by any method, including genetic engineering, using the genome of S. sonnei bacteria. Preferably the exopolysaccharide is produced using S. sonnei bacteria by a method, comprising: (a) producing bacterial culture in liquid phase; (b) separating the liquid phase from bacterial cells; and (c) isolating the polysaccharide from liquid phase. Meanwhile, in order to avoid destroying the cell walls and LPS entry into the liquid phase, separation from the bacterial cells is advisable to carry out under conditions for maintaining the nativity of bacterial cells. Isolating the polysaccharide from the liquid phase can be carried out by a method, comprising: (i) removing proteins and nucleic acids from the liquid phase; (ii) ultrafiltration, and (iii) dialysis of obtained solution.

The exopolysaccharide obtained by using the above method can contain no more than 1% (w/w) of protein and 2% (w/w) of nucleic acid. The molecular weight of the exopolysaccharide, which is measured by gel filtration, is from 0.4 to 400 kDa. The main fraction of the exopolysaccharide is a biopolymer with molecular weight over 80 kDa (FIG. 5B).

Exopolysaccharide is immunogenic and causes mucosal protection from *S. sonnei* shigellosis by inducing synthesis of specific antibodies against *S. sonnei*, phase I bacteria in mammalian organisms, including humans (Example 1C, FIG. 6; Examples 2D, 2F). Additionally, the exopolysaccharide is also a modulator of immune system response in mammals, including humans (Example 3B). The exopolysaccharide is apyrogenic for rabbits when administered intravenously at a dose of no more than 0.050 meg/kg in a rabbit pyrogenicity test (Example 1D).

The exopolysaccharide is apyrogenic for rabbits at a dose of no more than 0.050 mg/kg in a pyrogenicity test in rabbits when administered intravenously (Example 1D). The pharmaceutical composition is intended for parenteral, oral, rectal, intra-vaginal, transdermal, sublingual, and aerosol administration to mammals, including humans.

BRIEF DESCRIPTION OF DRAWINGS

The invention is illustrated by the following figures.

FIG. 1 shows the structural formula of the monomer unit of *S. sonnei*, phase I bacteria exopolysaccharide.

FIG. 2 shows C13 NMR-spectrum of *S. sonnei*, phase I bacteria exopolysaccharide.

FIG. 3 shows results of GC mass-spectrometry of *S. sonnei*, phase I bacteria LPS.

FIG. 4 shows results of GC mass-spectrometry of *S. sonnei*, phase I bacteria exopolysaccharide; arrows indicate non-hydroxylated fatty acid signals.

FIG. 5 shows graphs of molecular weight distribution of O-specific polysaccharide, isolated from *S. sonnei*, phase I bacteria (a) and *S. sonnei*, phase I bacteria exopolysaccharide (b). In this case, the vertical axis represents the values for ultraviolet absorption at a wavelength of 225 nm; the horizontal axis represents time in minutes.

FIG. 6 shows graphs of antibody production (15 days) after primary (a) and secondary (b) immunization of mice with preparations made with *S. sonnei*, phase I bacteria exopolysaccharides (lot 33) and O-polysaccharide from *S. sonnei*, phase I bacteria LPS, with dose of 25 micrograms per mouse. On the vertical axis are the values for serum titer dilution.

FIG. 7 shows graphs of binding of antibodies from rabbit monoreceptor serum to *S. sonnei*, phase I O-antigen, with samples: *S. sonnei* exopolysaccharide (lot 33 and 35); O-polysaccharide from *S. sonnei* bacteria cells LPS; *Salmonella enterica* sv *typhimurium* LPS; *S. flexneri* 2a LPS in ELISA test. On the horizontal axis shows the values of serum titer dilution and the vertical axis—the optical density of reaction color substrate (ortho-phenylenediamine) at a wavelength of 495/650 nm.

FIG. 8 shows a graph of antibody production (15 days) after primary (a) and secondary (b) immunization of mice with vaccine consisting of unconjugated form of *S. sonnei*, phase I bacterial exopolysaccharide and with vaccine of tetanus toxoid (TT) conjugated with *S. sonnei* bacteria exopolysaccharide phase I (lot 33), at a dosage of 25 micrograms of exopolysaccharides per mouse. The vertical axis shows values for serum titer dilution.

FIG. 9 shows graphs of survival rates of two groups of mice, infected with a dose of LD 100 of virulent influenza strain A subtype H1N1. The first group (experimental) received daily injections of the pharmaceutical composition, at a dose of 100 micrograms of exopolysaccharides per mouse, the second group (control)—injections of saline solution.

DETAILED DESCRIPTION OF THE PREFERRED EMBODIMENTS

Definitions

Altrpyranuronic acid. This term is derived from altruronic acid, which is a known composition in the art. Altruronic acid is derived from altrose (a well-known sugar) in which "ose" is replaced with "uronic acid," which indicates the corresponding acid compound rather than a sugar. The term "pyran" is inserted between the terms "altr" and "uronic acid" to indicate the ring size of the molecule. "Pyran" stands for a sixmembered ring. The compound named here corresponds to the chemical molecule shown in FIG. 1. The name has been derived using the IUPAC (International Union of Pure and Applied Chemistry) recommendations for nomenclature of carbohydrates (Joint Commission on Biochemical Nomenclature, reproduced from *Pure Appl. Chem.,* 1996, Pub. Elsevier Science Ltd.).

Nativity. A natural state or a unique set of physical, physiochemical, chemical, and biological properties of a cell, inherent in the natural state of a cell. Maintaining the nativity of a cell refers to keeping this unique set of properties with regard to the cell, including, but not limited to, using sparing regimens for precipitation and centrifugation of cells, not using chemical or physical treatments which result in the destruction of cells or cell parts, and removing LPS from given cells without disturbing their natural integrity.

Example 1

Preparation and Characteristics of *S. sonnei,* Phase I Bacteria Exopolysaccharide A. Exopolysaccharide Preparation Exopolysaccharide is prepared using *S. sonnei,* phase I bacteria. Bacteria culture prepared in liquid phase by deep cultivation of *S. sonnei* in nutrient medium. Separation of liquid phase from bacterial cells is performed by flow centrifuge (Westphalia) with cooling, in compliance with regimens for smooth deposition of cells while maintaining their cell nativity. Exopolysaccharide is isolated from the liquid phase by removing from it proteins and nucleic acids, followed by ultrafiltration and dialysis of obtained solution. For this purpose the liquid phase is concentrated and dialyzed using an installation for ultrafiltration (Vladisart, membrane exclusion limit 50 kDa). The dialysate is lyophilized, redissolved in 0.05 M Tris-buffer, pH=7.2, containing 0.01% CaCl2 and MgCl2, RNAse and DNAse is added in concentrations of 100 mcg/mL and 10 mcg/mL, respectively, and after 16 hours of stirring at 37° C. the reaction mixture is treated with proteinase K (20 mcg/mL) for 2 hours at 55° C. The resulting clear solution is subjected to ultrafiltration and dialysis using an installation for ultrafiltration (Vladisart, membrane exclusion limit 50 kDa). If necessary, the final solution may be lyophilized and purified exopolysaccharide, obtained with a yield of 60-80%. The exopolysaccharide obtained by the aforementioned method contains not more than 1% (w/w) protein, determined by the Bradford method (Bradford M. M. A rapid and sensitive method for the quantitation of microgram quantities of protein utilizing the principle of protein-dye binding. Anal. Biochem. 1976, v. 72, pp. 248-254), and not more than 2% (w/w) nucleic acid, determined by the Spirin method (Spirin A. S. Spectrophotometric determination of the total amount of nucleic acids. Biochemistry, 1958, v. 23, No 4, p. 656).

B. The Structure, Composition, and Physico-Chemical Properties of Exopolysaccharide The *S. sonnei,* phase I exopolysaccharide structure is studied using $C^{13}$ NMR spectroscopy. NMR-spectrometry performed by Bruker spectrometer, model DRX-500, with XWINNMR software and impulse sequences from the manufacturer. Survey of spectra are conducted in $D_{20}$ (99:95%) with acetone as a standard (31.5 ppm for $C^{13}$). High resolution mass-spectrometry with electrospray ionization and ion detection using ion-cyclotron resonance is performed on a Bruker Daltonics spectrometer, model Apex II, with 7 Tesla magnet.

Figure 2:
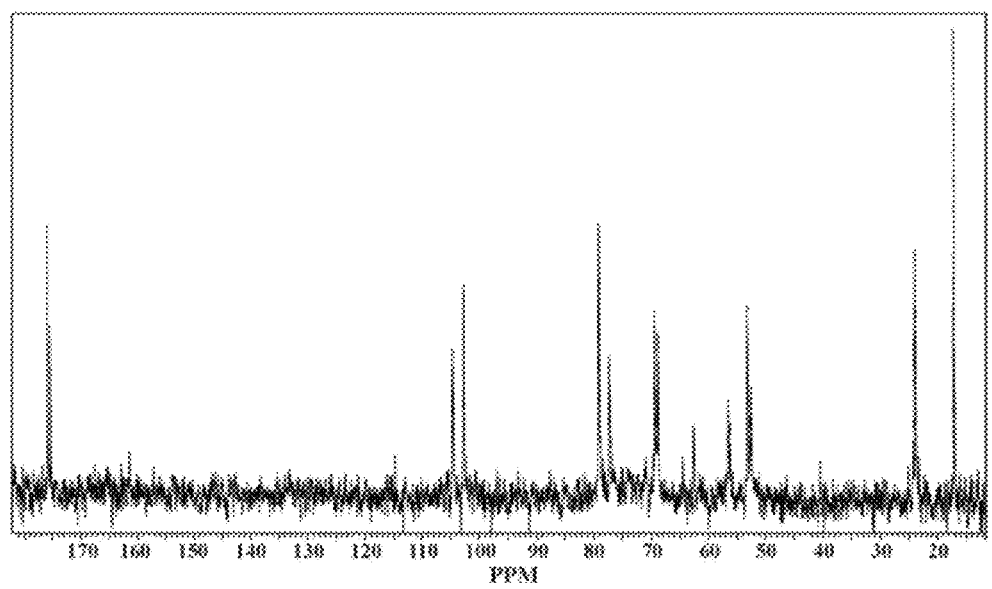

Comparative analysis of $C^{13}$ NMR-spectrum of exopolysaccharide (FIG. 2) shows it's full identity to known $C^{13}$ NMR-spectra of O-specific polysaccharide, isolated from LPS of *S. sonnei,* phase I, which clearly indicates identity of monomeric unit structure of both biopolymers (FIG. 1).

Studies of the exopolysaccharide's lipid component are carried out on the basis of fatty acid analysis using gas-liquid chromatography and GC/mass-spectrometry on a Hewlett Packard, model 5890 chromatograph, connected to a NERMAG, model R10-10L mass spectrometer.

Figure 3:
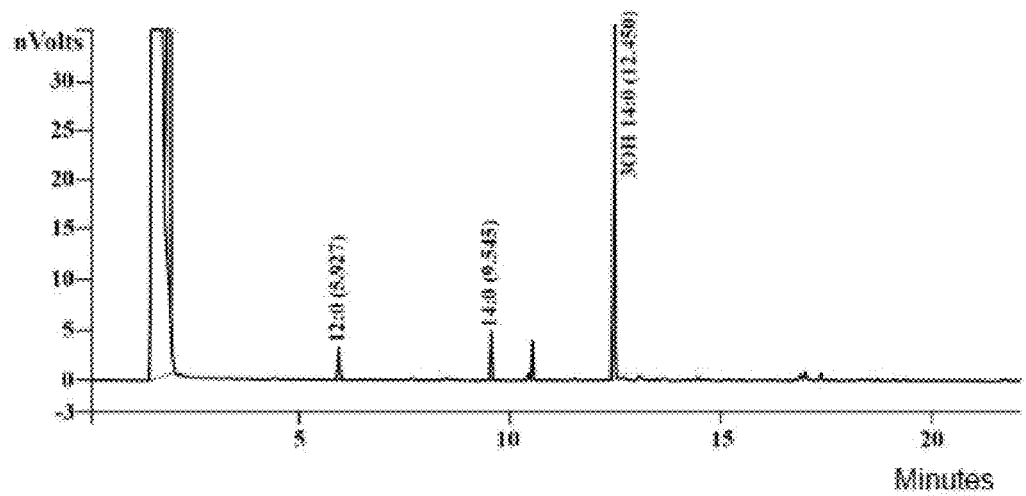

A comparative study of the fatty acid composition and exopolysaccharide structure and *S. sonnei,* phase I LPS is performed. Exopolysaccharide and LPS are subjected to methanolysis by treatment with 2M $HCl/CH_3OH$ at 85° C. for 16 hours. After methanolysis, among the products of LPS are lauric acid (12:0), myristic (14:0), and β-hydroxymyristic (30H14:0) acids (FIG. 3), whereas methanolysate of the exopolysaccharide contains, as basic products, methyl esters of higher fatty acids 16:0, 18:1, and 18:0.

The results of GC/mass spectrometry allow to conclude that the exopolysaccharide contains a non-toxic lipid component, composed of non hydroxylated fatty acids with 16-18 carbon atoms in the molecule, characteristic of diglycerides, in amounts no less than 0.01% (w/w). In exopolysaccharide, in contrast to LPS, oligosaccharide core components (heptose, Kdo) and lipid A (hydroxylated fatty acids, fatty acids with shorter chains than those of palmitic acid) were not found (FIG. 4).

Under mild acidic degradation of exopolysaccharide, cleavage of lipid part does not occur. Mild hydrolysis of LPS with 1% acetic acids leads to the removal of lipid A from LPS molecule. Meanwhile, the polysaccharide component obtained is an O-specific polysaccharide, linked to the core oligosaccharide (Fensom and Meadow, 1970; Morrison and Leive, 1975; Oertelt et al., 2001; Osborn, 1963).

Concluding, the exopolysaccharide is neither LPS, which must contain components core and lipid A domains, nor O-specific polysaccharide, which contains oligosaccharide fragment 'core'. It is rather a glycoconjugate with another composition and structure, but with the same repeating monomer unit structure as *S. sonnei* O-antigen.

Study of molecular weight distribution of *S. sonnei* exopolysaccharide and O-specific polysaccharide, isolated from *S. sonnei* LPS, is performed by HPLC on a TSK 3000 SW column with a flow-through UV detector (wavelength 225 nm) in a buffer, containing 0.02 M NaOAc, 0.2 M NaCl (pH 5.0). Comparative analysis of chromatograms of O-specific polysaccharide and exopolysaccharide show that the main fraction of the O-polysaccharide has a molecular weight of ~26 kDa (FIG. 5A), whereas the exopolysaccharide is a biopolymer with a molecular weight exceeding 80 kDa (FIG. 5B).

C. Exopolysaccharide Immunogenicity

Two groups of mice strain (CBAXC57Bl/6) F1 are immunized intraperitoneally with *S. sonnei,* phase 1 bacteria exopolysaccharide drug preparation, lot 33, and O-polysaccharide preparation from *S. sonnei,* phase 1 bacterial cell LPS, with a dose of 25 micrograms per mouse. Exopolysaccharide drug preparation induces humoral immune response after a single dose injection and at day 15 the peripheral blood sera of animals is shown 3.4-fold increase in IgG antibodies; the O-polysaccharide preparation from bacterial cell LPS induces weak primary immune response—1.9-fold rise in of IgG antibodies levels on day 15, in comparison (FIG. 6A).

To study secondary immune response the same groups of mice are reimmunized with antigens at a dose of 25 micrograms per mouse a month after primary injection. On day 15, secondary response occurs after repeated immunization with exopolysaccharide drug preparation, lot 33, 25-fold rise of IgG anti-O antibodies registered in mice, i.e. anamnestic secondary immune response is observed. After reimmunization with O-polysaccharide preparation from bacterial cell LPS, a low 3.4-fold increase in IgG anti-O antibodies is recorded in mice (FIG. 6). Thus, bacterial exopolysaccharide is much more immunogenic, inducing the synthesis of O-specific IgG antibodies, which has a level 7 times higher than that induced by the O-polysaccharide of bacterial cell LPS.

D. Exopolysaccharide Pyrogenicity

The pyrogenicity of S. sonnei bacteria exopolysaccharide drug preparation (lot 33 and 35) and O-polysaccharide from S. sonnei bacterial cell LPS is determined in comparison with pyrogenicity of LPS samples, extracted from cells of the same strain by the Westphal method (Westphal O., Jann K. Bacterial lipopolysaccharide extraction with phenol: water and further application of the procedure. Methods Carbohydr. Chem., 1965, v. 5, pp. 83-91), and with commercial Vi-antigen vaccine. The test is conducted on Chinchilla rabbits weighing 2.8-3.05 kg in accordance with requirements of WHO Technical Regulations for Vi-polysaccharide vaccines (WHO Technical report No. 840, 1994). After administration of sample, rabbit rectal temperature was measured three times at 1 hour intervals. A preparation is considered apyrogenic if total temperature increase does not exceed 1.15° C.

TABLE 1

Pyrogenicity of polysaccharide preparations and LPS from S. sonnei bacteria and commercial Vi-antigen vaccine

| Preparation | Temperature increase, in ° C. | Pyrogenicity |
|---|---|---|
| Vi-antigen typhoid vaccine «Vianvac», lot 152 | (0.1; 0.2; 0.3) Σ: 0.6 | apyrogenic |
| Exopolysaccharide from S. sonnei bacteria, lot 33 | (0.2; 0.2; 0.1) Σ: 0.5 | apyrogenic |
| Exopolysaccharide from S. sonnei bacteria, lot 35 | (0.2; 0.2; 0.3) Σ: 0.7 | apyrogenic |
| O-polysaccharide from LPS of S. sonnei bacteria cells | (0.2; 0.1; 0.2) Σ: 0.5 | apyrogenic |
| LPS from the cells of S. sonnei bacteria | (1.1; 0.8; 1.0) Σ: 2.9 | high pyrogenicity |

Intravenous administration of S. sonnei bacterial exopolysaccharide drug preparation and O-polysaccharide from S. sonnei bacterial cell LPS at doses of 0.050 mcg per kg of body weight do not cause pyrogenic effect in rabbits. LPS preparation, extracted from cells of the same strain, being a classic endotoxin, demonstrated high pyrogenicity.

Example 2

Vaccines, Comprising of S. sonnei, Phase I Bacterial Exopolysaccharide

B. Use of the Exopolysaccharide for Production of Unconjugated Vaccine (Pharmaceuticals)

Preparation of unconjugated vaccine includes obtaining exopolysaccharide using S. sonnei, phase I bacteria in accordance with Example 1 (A) and subsequent aseptic filling of vials or syringes with solution containing the active substance and pharmaceutically suitable special additives, which may include pH stabilizers, preservatives, adjuvants, isotonizing agents, or combinations thereof. Vaccination dose contains: unconjugated form of exopolysaccharide, in amount from 0.010 mg to 0.100 mg; phenol (preservative), not exceeding 0.75 mg (Sigma, USP Grade 108-95-2), with addition of sodium chloride (Sigma, USP Grade 7647-14-5), dibasic sodium phosphate (Sigma, USP Grade 7782-85-6), and monobasic sodium phosphate (Sigma, USP Grade 13472-35-0); and sterile pyrogen-free water for injection, 0.5 mL (FS 42-2620-97, EP IV 2002).

B. Serological Activity of Unconjugated Vaccine

Serological activity and immune specificity of vaccine, including of exopolysaccharide in unconjugated form, in concentration of 100 mcg/mL (lots 33 and 35), were determined in inhibition passive hemagglutination reaction (IHA) in comparison with other O-antigens samples in concentration of 100 mcg/mL—O-polysaccharide from LPS of S. sonnei bacteria cells, as well as LPS's from S. sonnei, S. flexneri 2a, and Salmonella enterica sv typhimurium, obtained by Westphal method (Westphal O., Jann K. Bacterial lipopolysaccharide extraction with phenol: water and further application of the procedure. Methods Carbohydr. Chem., 1965, v. 5, p. 83-91). Commercial diagnostic kit contains *S. sonnei* antigen adsorbed erythrocytes (Microgen, Russia) and mono-receptor rabbit antiserum to *S. sonnei* O-antigen is used.

IHA concentration by vaccine, which includes exopolysaccharide (lots 33 and 35), O-polysaccharide from LPS, as well as *S. sonnei* bacterial LPS preparation, did not exceed 1.56 mcg/mL (Table 2). Heterologous bacterial LPS's of *S. flexneri* 2a and *Salmonella enterica* sv *typhimurium* had low serological activity in the IHA reaction with *S. sonnei* monoreceptor serum (inhibition concentration ≥25 mcg/mL) (Table 2).

TABLE 2

IHA inhibition by unconjugated vaccine, includes exopolysaccharide *S. sonnei* bacteria, and preparations of O-polysaccharide from LPS of *S. sonnei* bacteria cells and LPS's from *S. sonnei*, *S. flexneri* 2a, *Salmonella enterica* sv *typhimurium* bacteria

| Preparation | IHA concentration, mcg/mL |
|---|---|
| Vaccine, includes of *S. sonnei* bacteria exopolysaccharide in unconjugated form (lot 33-1) | 1.56 |
| Vaccine, includes of *S. sonnei* bacteria exopolysaccharide in unconjugated form (lot 35-1) | 0.78 |
| O-polysaccharidefrom LPS of *S. sonnei* bacteria cells | 1.56 |
| LPS of *S. sonnei* bacteria | 0.78 |
| LPS of *S. flexneri* 2a bacteria | 25.00 |
| LPS of *Salmonella enterica* sv *typhimurium* bacteria | >25.0 |

Interaction of in vitro the vaccine lots, includes unconjugated exopolysaccharide of *S. sonnei* bacteria at concentrations of 100 mcg/mL (lots 334 and 35-1), and other O-antigens in concentrations of 100 mcg/mL—O-polysaccharide from LPS of *S. sonnei* bacteria cells, preparation of LPS from *S. flexneri* 2a and *Salmonella enterica* sv *typhimurium* bacteria, with rabbit mono-receptor serum antibodies to *S. sonnei* O-antigen is detected in ELISA test. Under solid phase absorption, the vaccine, includes of *S. sonnei* bacterial exopolysaccharide and O-polysaccharide sample from *S. sonnei* bacterial cell LPS, effectively interacted with *S. sonnei* O-antigen antiserum (FIG. 7).

C. Pyrogenicity of Unconjugated Vaccine

Pyrogenicity of vaccine, containing 100 mcg/mL of *S. sonnei* bacteria exopolysaccharide in the unconjugated form (lots 33 and 35), is determined in comparison with pyrogenicity of commercial Vi-antigen vaccine, O-polysaccharide from LPS of *S. sonnei* bacteria cells and LPS's isolated from cell culture supernatant and cells of the same strain using the Westphal method described in Example 1C. Test results are shown in Table 3.

TABLE 3

Pyrogenicity of the vaccine, containing S. sonnei bacteria
exopolysaccharide in the unconjugated form, commercial
Vi-antigen vaccine, preparations of O-polysaccharide from
LPS of S. sonnei bacteria cells and LPS's of S. sonnei bacteria

| Preparation | Temperature increase, ° C. | Pyrogenicity |
|---|---|---|
| Vi-antigen typhoid vaccine «Vianvac», lot 152 | (0.3; 0.2; 0.0) Σ: 0.5 | apyrogenic |
| Vaccine, includes exopolysaccharide from S. sonnei bacteria, (lot 33-1) | (0.2; 0.2; 0.2) Σ: 0.6 | apyrogenic |
| Vaccine, containing exopolysaccharide from S. sonnei bacteria, (lot 35-1) | (0.2; 0.1; 0.3) Σ: 0.6 | apyrogenic |
| O-polysaccharide from LPS of S. sonnei bacteria cells | (0.1; 0.1; 0.3) Σ: 0.5 | apyrogenic |
| LPS from supernatant of S. sonnei bacteria culture | (1.2; 1.2; 1.1) Σ: 3.5 | highly pyrogenic |
| LPS from S. sonnei bacteria cells | (1.1; 0.9; 1.1) Σ: 3.1 | highly pyrogenic |

Intravenous administration of vaccine, includes of S. sonnei bacteria exopolysaccharide, at a dose of 0.050 mcg per kg body weight does not cause pyrogenic effect in rabbits. Preparation containing LPS from S. sonnei bacteria cells of the same strain shows high pyrogenicity and thus represents a classic endotoxin.

D. Protective Properties of Unconjugated Vaccine

To study formation of protective mucosal immunity in guinea pigs, laboratory animals weighing 200-250 g are immunized with subcutaneous injection of vaccine, including 100 mcg/mL of unconjugated form of S. sonnei bacterial exopolysaccharide (lots 33 and 35) and a preparation of O-polysaccharide from LPS of S. sonnei bacteria cells, in doses of 25 and 50 mcg per animal, twice in the back region with 10 day interval. Control animals are given saline instead of the preparation. Ten days after the last immunization, S. sonnei kerato-conjunctivitis (Sereny test) is induced in the experimental and control animals by introduction into the eye conjunctiva cell suspension of virulent strain of S. sonnei in a dose, close to $ID_{100}$ ($10^9$ cells), and in a dose close to $2ID_{100}$ ($2 \times 10^9$ cells), in 30 mcL of sterile saline. All control group animals, infected with a dose of $2 \times 10^9$ cells, and 90% of control group animals, infected with a dose of $10^9$ cells, developed S. sonnei kerato-conjunctivitis (Table 4). Immunization with vaccine, including exopolysaccharide (lots 33 and 35), in a dose of 25 mcg provides an eye protection rate of 70-90% of experimental animals infected with a dose of $10^9$ cells; when infected with $2 \times 10^9$ cells dose, the eye protection rate varies from 50% to 70%, respectively. A higher dose of 50 mcg immunization with the same vaccine provides an eye protection rate of 55% to 85% in experimental animals infected with a dose of $10^9$ cells; when infected with $2 \times 10^9$ cells dose, eye protection level varies from 50% to 70%, respectively. Thus, under subcutaneous immunization of the animals with vaccine based on unconjugated form of S. sonnei bacterial exopolysaccharide (lots 33 and 35), a marked local anti-Shigella immunity is registered, meanwhile immunization with preparation of O-polysaccharide from LPS of S. sonnei bacterial cells does not show anti-Shigella effect of the preparation.

TABLE 4

Protective mucosal immunity to infection S. sonnei in guinea pigs as a result
of the systemic immunization with vaccine, based on unconjugated form
of S. sonnei bacteria exopolysaccharide

| Preparation | Preparation dose, mcg per animal | Infection dose (No. of cells in 30 mcL of saline solution) | No. of infected animals | No. of infected eyes | No. of eyes with kerato-conjunctivitis | No. of eyes protected from kerato-conjunctivitis | Rate of the eye protection, % |
|---|---|---|---|---|---|---|---|
| Vaccine, containing exopolysaccharide from S. sonnei bacteria, (lot 33) | 25 | 109 | 10 | 20 | 2 | 18 | 90 |
| | 25 | 2 × 109 | 10 | 20 | 6 | 14 | 70 |
| | 50 | 109 | 10 | 20 | 9 | 11 | 55 |
| | 50 | 2 × 109 | 10 | 20 | 10 | 10 | 50 |
| Vaccine, containing exopolysaccharide from S. sonnei bacteria (lot 35) | 25 | 109 | 10 | 20 | 6 | 14 | 70 |
| | 25 | 2 × 109 | 10 | 20 | 10 | 10 | 50 |
| | 50 | 109 | 10 | 20 | 3 | 17 | 85 |
| | 50 | 2 × 109 | 10 | 20 | 6 | 14 | 70 |
| O-polysaccharide from LPS of S. sonnei bacteria cells | 25 | 109 | 10 | 20 | 12 | 4 | 20 |
| | 25 | 2 × 109 | 10 | 20 | 14 | 6 | 0 |
| | 50 | 109 | 10 | 20 | 16 | 4 | 10 |
| | 50 | 2 × 109 | 10 | 20 | 17 | 3 | 15 |
| Control | — | 109 | 10 | 20 | 18 | 2 | 10 |
| | — | 2 × 109 | 10 | 20 | 20 | 0 | 0 |

E. Safety of Unconjugated Vaccine

Vaccine, including the unconjugated form of S. sonnei bacterial exopolysaccharide (lot 33), in a dose of 50 mcg of antigen, contained in 0.5 mL of phenol-phosphate buffer solution, and the preparation for comparison—typhoid Vi-antigen vaccine "Vianvac", in a dose of 25 mcg, are single injected subcutaneously into two groups of 20 adult volunteers in the upper third of the shoulder. Temperature reactions to the drug injection, general side effects and local reactions of volunteers are studied for the first three days after immunization. Vaccine, comprising *S. sonnei* bacterial exopolysaccharide (lot 33), administered in 50 mcg doses, shows high safety profile for adult volunteers. Temperature reactions in the 37.1-37.5° C. range are found in only 5% of volunteers, higher temperature reactions and general side effects are absent; local reaction (pain at injection site) is detected in only one volunteer (Table 5).

TABLE 5

Safety of the vaccine, including the unconjugated form of *S. sonnei* bacterial exopolysaccharide under immunization of the adult volunteers

| Reactions on vaccine administration | Vaccine, containing exopolysaccharide from *S. sonnei* bacteria (lot 33), 50 mcg dose | Vi-antigen vaccine «Vianvac» (lot 193), 25 mcg dose |
|---|---|---|
| Temperature reactions (37.1-37.5° C.) | 5% of volunteers | 5% of volunteers |
| Temperature reactions (37.6-38.5° C.) | absent | Absent |
| Temperature reactions (38.5° C. and up) | absent | Absent |
| Side effects | absent | Absent |
| Local reactions (pain) | one case | one case |

F. Immunogenicity of Unconjugated Vaccine

Immunogenicity of vaccine, including unconjugated *S. sonnei* bacterial exopolysaccharide (lot 33), for adult volunteers is determined in serological studies using the following tests: enzyme-linked immunosorbent analysis (ELISA) and passive hemagglutination reaction (PHA). Vaccines, comprising *S. sonnei* bacterial exopolysaccharide (lot 33), in a dose of 50 mcg of antigen, contained in 0.5 mL of phenol-phosphate buffer solution, and the preparation for comparison—typhoid Vi-antigen vaccine "Vianvac", in 25 mcg dose, are single injected subcutaneously into two groups of 20 adult volunteers in the upper third of the shoulder. Blood sera for testing are taken from each subject before vaccination and 30 and 60 days after vaccination. To perform ELISA analysis, microplates coated with *S. sonnei* bacterial exopolysaccharide, rabbit antibodies against human IgG, IgM, IgA, conjugated with horseradish peroxidase (Sigma, USA) are used. The optical density is measured on a Bio-Rad iMark ELISA-reader under dual wavelength readings (490/630 nm). PHA test is performed according to manufacturer's instructions, using *S. sonnei* commercial erythrocyte diagnosticum (Microgen, Russia).

Immunogenicity is evaluated according to following criteria: 4-fold seroconversion compared to background serum, level of antigenic response before and after vaccination; also, geometric mean antibody titer (GM) is measured, titers fold rise in vaccinated group in comparing with background sera levels.

The increase in anti-O antibody titers is observed in all volunteers who are given vaccine with *S. sonnei* bacterial exopolysaccharide (lot 33). High rises in agglutinating antibody titer before and after vaccination are registered; with 40.7× and 42.5× fold rise on the 30th and 60th days after vaccination, respectively. High levels of seroconversion of antibodies to *S. sonnei* O-antigen, comprising ≥90% is registered among vaccinated subjects. In subjects immunized with "Vianvac" vaccine, rises in specific antibodies to exopolysaccharide and 4-fold seroconversions are not observed (Table 6).

High rises of antibody titers, especially IgA class, are revealed under the fold rise and seroconversion study of IgA, IgG, IgM classes of antibodies to *S. sonnei* O-antigen in ELISA test, compared to background level, among subjects immunized with vaccine, comprising *S. sonnei* bacterial exopolysaccharide (lot 33). Thus, the rise of titer IgA antibodies on the 30th and 60th day after immunization was 25.7-fold and 30.2-fold, respectively; IgG antibodies—6.1-fold and 5.8-fold, respectively. Seroconversion rate of O-specific antibody IgA, IgG classes is high and consists of 95% and 95% for IgA; 75% and 70% for IgG, on the 30th and 60th days after vaccination, respectively. Therefore, the claimed vaccine, comprising unconjugated *S. sonnei* bacteria exopolysaccharide, under a single subcutaneous immunization of adult volunteers, induces human systemic adaptive immune response with dominating antibody of IgA class.

TABLE 6

Induction systemic immune response in adult volunteers under a subcutaneous immunization by vaccine, comprising unconjugated *S. sonnei* bacteria exopolysaccharide

| Vaccine and the immunization dose | No. of volunteers | Antibody titer fold rise in comparison with antigen titer before vaccination | % of volunteers with 4-x fold seroconversion 30 days after vaccination | Antibody titer fold rise in comparison with antigen titer before vaccination | % of volunteers with 4-x fold seroconversion 60 days after vaccination |
|---|---|---|---|---|---|
| PHA test-agglutinating antibodies | | | | | |
| Vaccine, includes exopolysaccharide from *S. sonnei* bacteria, (lot 33), 50 mcg | 20 | 40.7 | 90% | 42.5 | 95% |
| Vi-antigen vaccine «Vianvac» (lot 193), 25 mcg | 20 | 1.14 | None | 1.16 | None |
| ELISA test - IgA | | | | | |
| Vaccine, includes exopolysaccharide from *S. sonnei* bacteria, (lot 33), 50 mcg | 20 | 25.7 | 95% | 30.2 | 95% |

TABLE 6-continued

Induction systemic immune response in adult volunteers under a subcutaneous immunization by vaccine, comprising unconjugated *S. sonnei* bacteria exopolysaccharide

| Vaccine and the immunization dose | No. of volunteers | Antibody titer fold rise in comparison with antigen titer before vaccination | % of volunteers with 4-x fold seroconversion 30 days after vaccination | Antibody titer fold rise in comparison with antigen titer before vaccination | % of volunteers with 4-x fold seroconversion 60 days after vaccination |
|---|---|---|---|---|---|
| Vi-antigen vaccine «Vianvac» (lot 193), 25 mcg | 20 | 0.82 | None | 0.99 | None |
| ELISA test - IgG ||||||
| Vaccine, includes exopolysaccharide from *S. sonnei* bacteria, (lot 33), 50 mcg | 20 | 6.1 | 75% | 5.8 | 70% |
| Vi-antigen vaccine «Vianvac» (lot 193), 25 mcg | 20 | 1.06 | None | 1.09 | None |
| ELISA test - IgM ||||||
| Vaccine, includes exopolysaccharide from *S. sonnei* bacteria, (lot 33), 50 mcg | 20 | 2.51 | 50% | 2.73 | 50% |
| Vi-antigen vaccine «Vianvac» (lot 193), 25 mcg | 20 | 1.10 | None | 1.14 | None |

G. Use of the Exopolysaccharide for Production of Conjugated Vaccine (Pharmaceuticals)

The exopolysaccharide is obtained using *S. sonnei* bacteria, phase in accordance with Example 1 (A). Obtaining conjugate of exopolysaccharide with protein can be performed by any of the known methods. In the framework of this study, the method used (Taylor D. N., Trofa A. C., Sadoff J., Chu C., Brula D., Shiloach J., Cohen D., Ashkenazi S., Lerman Y., Egan W., Schneerson R., Robbins J. B. Synthesis, characterization, and clinical evaluation of conjugate vaccines composed of the O-specific polysaccharides of *Shigella dysenteriae* type 1, *Shigella flexneri* type 2a, and *Shigella sonnei* (*Plesiomonas shigelloides*) bound to bacterial toxoids. Infect. and Immunity. 1993, pp. 3678-3687), can be described as based on modification of exopolysaccharide by adipic dihydrazide (ADH) in the presence of 1-ethyl-3-(3-dimethylaminopropyl)carbodiimide (CDI) followed by reaction of the resulting amidated exopolysaccharide with a free hydrazide group with protein carrier—tetanus toxoid (TT).

Modification of exopolysaccharide with ADH in the presence of CDI is performed in water for 2-16 hours, keeping the pH between 4.8-5.2 by adding HCl concentrate with a pH-stat. Modified exopolysaccharide is separated on a column by Sephadex G-50 in water. Control of amidation levels is performed using $C^{13}$-NMR spectroscopy. Conjugation of modified exopolysaccharide with tetanus toxoid is carried out in 0.2 M sodium chloride solution in the presence of CDI for 4-18 hours, while maintaining pH 5.6 using the pH-stat. Conjugate is purified on column with Sepharose CL-6B from insignificant amounts of unconjugated biopolymers and impurities with low molecular weight, using 0.2M of sodium chloride solution as an eluent. Fractions, containing conjugate of the EPS with protein and eluted near the column void volume, are combined and phenol is added to a concentration of 0.05-0.15% for subsequent filling in sterile vials with addition of pharmaceutically suitable special additives, which include pH stabilizers or preservatives, adjuvants, isotonizing agents, or combinations thereof.

The conjugate vaccine contains 40% protein mass, determined by the Bradford method (Bradford M. M. A rapid and sensitive method for the quantitation of microgram quantities of protein utilizing the principle of protein-dye binding. Anal. Biochem. 1976, v. 72, pp. 248-254). One vaccination dose of conjugated vaccine contains: exopolysaccharide conjugate from 0.010 to 0.200 mg; phenol (preservative), not to exceed 0.75 mg (Sigma, USP Grade 108-95-2), with addition of sodium chloride (Sigma, USP Grade 7647-14-5), dibasic sodium phosphate (Sigma, USP Grade 7782-85-6), and monobasic sodium phosphate (Sigma, USP Grade 13472-35-0); and 0.5 mL sterile pyrogen-free water for injection (FS 42-2620-97, EP IV 2002).

H. Conjugate Vaccine Immunogenicity

Figure 8:
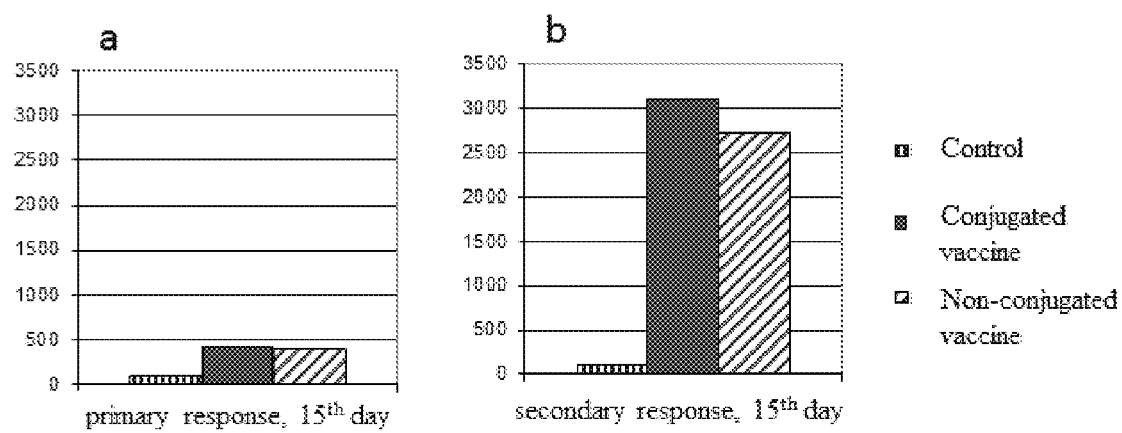

Two groups of mice (CBAXC57Bl/6) F1 are intraperitoneally immunized with a vaccine, comprising unconjugated *S. sonnei* bacterial exopolysaccharide, lot 33 and a vaccine, comprising conjugate *S. sonnei* bacterial exopolysaccharide, lot 33 with a TT carrier protein, at a dose of 25 mcg of polysaccharide per mouse. Unconjugated vaccine after a single dose immunization induces humoral immune response and a 3.4-fold increase in IgG antibodies is detected at day 15 in the peripheral blood serum of animals. Conjugate vaccine also induces a humoral immune response after a single dose injection and a 3.7-fold increase in IgG antibodies was detected at day 15 in the peripheral blood serum of animals (FIG. 8A).

To study secondary immune response, the same groups of mice are vaccinated again with a dose of 25 mcg of polysaccharide per mouse a month after primary injection. On day 15 of the secondary response after second immunization with conjugate vaccine, a 27-fold rise of IgG anti-O antibodies is registered, and after the second immunization with unconjugated vaccine—a 23.6-fold rise of IgG anti-O antibodies. Under this experiment, the levels of O-specific antibodies significantly exceed the primary immune response antibody levels in immunized mice (FIG. 8B).

Example 3

Pharmaceutical Composition Comprising *S. sonnei*, Phase I Bacterial Exopolysaccharide A. Use of the Exopolysaccharide for Production of Pharmaceutical Compositions (Pharmaceuticals).

Preparation of a pharmaceutical composition comprises obtaining the exopolysaccharide using *S. sonnei*, phase 1 bacteria in accordance with Example 1 (A) and subsequent filling into sterile vials or syringes of solution containing the active substance and pharmaceutically suitable special additives, which can include preservatives, stabilizers, solvents, or a combination thereof.

A therapeutic dose of a pharmaceutical composition comprises: exopolysaccharide, from 0.010 to 5,000 mg, with the addition of sodium chloride (Sigma, USP Grade 108-95-2), dibasic sodium phosphate (Sigma, USP Grade 7782-85-6), monobasic sodium phosphate (Sigma, USP Grade 13472-35-0), and 0.5 mL sterile pyrogen-free water for injection (FS 42-2620-97, EP IV 2002).

B. The Antiviral Effect of Pharmaceutical Compositions

Two groups of mice (CBAXC57Bl/6)F1, 10 animals each, are infected with LD100 dose of virulent strain of influenza A subtype H1N1, after which the experimental group is treated with daily intraperitoneal administration of pharmaceutical composition to animals at a dose of 100 mcg of exopolysaccharide per animal; the control group of animals is similarly injected with saline. Animal survival rate is determined in the two weeks after infection. In the control group, the survival rate is 0%, in the experimental group—20% (FIG. 9). The mean survival time of the experimental group of mice is statistically significantly ($p<0.001$) higher than for mice of the control group. Thus, the experimental data show that the claimed pharmaceutical composition has a modulating effect on immune response.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A pharmaceutical composition, comprising: an effective amount of a polysaccharide, the polysaccharide being *Shigella sonnei*, phase I polysaccharide, comprising: 1-100 repeating disaccharide units of O-[4-amino-2-(N-acetyl) amino-2,4-dideoxy-β-D-galactopyranosyl]-(1→4)-O-[2-(N-acetyl)amino-2-deoxy-α-L-altrpyranuronic acid] linked within the polysaccharide chain by (1→3) bonds, produced using *S. sonnei* bacteria, but without using lipopolysaccharides as a source of production, further comprising non-hydroxylated fatty acids.

2. The pharmaceutical composition according to claim 1, wherein the polysaccharide contains a non-toxic lipid component.

3. The pharmaceutical composition according to claim 2, wherein the polysaccharide has, as the non-toxic lipid component, non-hydroxylated fatty acids having 16-18 carbon atoms per molecule.

4. The pharmaceutical composition according to claim 3, wherein an amount of non-hydroxylated fatty acids in the polysaccharide is no less than 0.01 (w/w) percent.

5. The pharmaceutical composition according to claim 1, wherein the polysaccharide has molecular weight, measured by gel-filtration method, from 0.4 to 400 kDa.

6. The pharmaceutical composition according to claim 1, wherein the polysaccharide contains no more than 1 (w/w) percent of protein and 2 (w/w) percent of nucleic acids.

7. The pharmaceutical composition according to claim 1, further comprising pharmaceutically acceptable additives selected from a group, comprising preservatives, stabilizers, solvents, and their combinations.

8. The pharmaceutical composition according to claim 1, wherein the composition is in a form of a vaccine, further comprising pharmaceutically acceptable additives.

9. The pharmaceutical composition according to claim 8, wherein the pharmaceutically acceptable additives are selected from a group, comprising pH stabilizers, preservatives, adjuvants, isotonizing agents, and their combinations.

10. The pharmaceutical composition according to claim 9, further comprising the polysaccharide in a non-conjugated form.

11. The pharmaceutical composition according to claim 8, further comprising a carrier protein as the pharmaceutically acceptable additive.

12. The pharmaceutical composition according to claim 11, wherein the carrier protein is selected from a group comprising diphtheria toxoid, tetanus toxoid, and *Pseudomonas aeruginosa* exoprotein A.

13. The pharmaceutical composition according to claim 11, further comprising the polysaccharide in a conjugated form.

14. The pharmaceutical composition according to claim 1, wherein the polysaccharide is in a form of an exopolysaccharide, secreted by *S. sonnei*, phase I bacteria, into an external medium.

15. The pharmaceutical composition according to claim 1, wherein the polysaccharide is in a form of a bacterial capsular polysaccharide.

16. A pharmaceutical composition, comprising: an effective amount of a polysaccharide, the polysaccharide being *Shigella sonnei*, phase I polysaccharide, comprising: 1-100 repeating disaccharide units of O-[4-amino-2-(N-acetyl) amino-2,4-dideoxy-β-D-galactopyranosyl]-(1→4)-O-[2-(N-acetyl)amino-2-deoxy-α-L-altrpyranuronic acid] linked within the polysaccharide chain by (1→3) bonds, further comprising non-hydroxylated fatty acids.

* * * * *